United States Patent
Federici

(10) Patent No.: US 7,986,413 B2
(45) Date of Patent: Jul. 26, 2011

(54) METHODS AND APPARATUS FOR RAPID SCANNING CONTINUOUS WAVE TERAHERTZ SPECTROSCOPY AND IMAGING

(75) Inventor: John Francis Federici, Westfield, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 158 days.

(21) Appl. No.: 12/353,742

(22) Filed: Jan. 14, 2009

(65) Prior Publication Data

US 2009/0180122 A1 Jul. 16, 2009

Related U.S. Application Data

(60) Provisional application No. 61/020,765, filed on Jan. 14, 2008.

(51) Int. Cl.
*G01B 9/02* (2006.01)
*G01J 3/45* (2006.01)

(52) U.S. Cl. ........................ 356/456; 356/485
(58) Field of Classification Search .................. 356/484, 356/485, 451, 456
See application file for complete search history.

(56) References Cited

U.S. PATENT DOCUMENTS

| | | | |
|---|---|---|---|
| 5,623,145 A * | 4/1997 | Nuss | 250/330 |
| 5,952,818 A * | 9/1999 | Zhang et al. | 324/96 |
| 6,057,928 A * | 5/2000 | Li et al. | 356/445 |
| 6,111,416 A * | 8/2000 | Zhang et al. | 324/753 |
| 6,605,808 B2 * | 8/2003 | Mickan et al. | 250/341.8 |
| 6,665,075 B2 * | 12/2003 | Mittleman et al. | 356/450 |
| 6,734,974 B2 * | 5/2004 | Jiang et al. | 356/432 |
| 6,815,683 B2 * | 11/2004 | Federici et al. | 250/341.1 |
| 7,119,339 B2 * | 10/2006 | Ferguson et al. | 250/358.1 |
| 7,129,491 B2 * | 10/2006 | Ferguson et al. | 250/341.1 |
| 2002/0074500 A1 * | 6/2002 | Mickan et al. | 250/341.8 |
| 2002/0153874 A1 * | 10/2002 | Jiang et al. | 324/96 |
| 2004/0065831 A1 * | 4/2004 | Federici et al. | 250/341.1 |
| 2005/0023470 A1 * | 2/2005 | Ferguson et al. | 250/358.1 |
| 2005/0253071 A1 * | 11/2005 | Ferguson et al. | 250/341.1 |
| 2009/0180122 A1 * | 7/2009 | Federici | 356/451 |
| 2010/0001189 A1 * | 1/2010 | Federici | 250/340 |

* cited by examiner

*Primary Examiner* — Patrick J Connolly
(74) *Attorney, Agent, or Firm* — Timothy X. Gibson, Esq.; Gibson & Dernier LLP

(57) ABSTRACT

Methods and apparatus are provided employing rapid scanning continuous wave terahertz spectroscopy and imaging for the non-destructive evaluation of materials such as animal hides and natural cork, and explosive detection, concealed weapon detection, and drug detection. A system employing an aperiodic detector array and implementing phase modulation at 100 kHz significantly reduces the imaging time and enables interferometric images of a THz point source to be obtained at several frequencies between 0.3 and 0.95 THz.

17 Claims, 6 Drawing Sheets

A                                   B

METHODS AND APPARATUS FOR RAPID SCANNING CONTINUOUS WAVE TERAHERTZ SPECTROSCOPY AND IMAGING

CROSS-REFERENCE TO RELATED APPLICATIONS

This application claims the benefit of U.S. Provisional Patent Application No. 61/020,765, filed Jan. 14, 2008, the entirety of which is incorporated herein by reference.

GOVERNMENT RIGHTS

The research leading to the present invention was supported, in part by the Department of Defense's Technical Service Work Group (TSWG) through a contract (N41756-04-C-4163) and by the U.S. Army through a contract (DAAE3003D1015-18). Accordingly, the United States Government may have certain rights in the invention.

FIELD OF THE INVENTION

This invention relates to methods and apparatus for performing terahertz (also referred to herein as "THz") spectroscopy and imaging. More specifically, the invention relates to methods and apparatus employing rapid scanning continuous wave terahertz spectroscopy for the non-destructive evaluation of materials such as animal hides and natural cork, and explosive detection, concealed weapon detection, and drug detection.

BACKGROUND OF THE INVENTION

Electromagnetic radiation in the THz frequency lies between the far infrared (which is generated by optical means) and microwave (which is generated by electrical means) regions of the electromagnetic spectrum. Because THz waves lie at the edge of the capabilities of both electrical and optical wave generation techniques, it was previously difficult, if not impossible, to generate THz waves needed for THz spectroscopy. Advances in the art have been able to produce radiation in the THz spectrum that could be used for THz spectroscopy. THz radiation is readily transmitted through most non-metallic and non-aqueous mediums, thus enabling THz systems to "see through" concealing barriers such as plastic packaging, corrugated cardboard, clothing, shoes, book bags, glass, etc. in order to probe the materials contained within (see, J. F. Federici et al., *Semicond. Sci. Technol.* 20 S266-S280 (2005); J. E. Bjarnason, et al., *Appl. Phys. Lett.*, 85, 519 (2004)) while posing minimal or no risk to human health. Therefore, THz radiation is attractive for routine screening of people or animals. In addition, explosives and other dangerous agents have characteristic absorption spectra in the THz frequency range (see, W. R. Tribe et al., *Proc. SPIE* 5354 168 (2004); F. Huang et al., *Appl. Phys. Lett.*, 85, 5535 (2004); H. Liu et al., *Opt. Express* 14, 415 (2006)), providing for THz waves a unique opportunity to distinguish these materials by their spectral signatures even if they are concealed behind barriers.

In 1995, Hu and Nuss demonstrated the first THz images. See, B. B. Hu and M. C. Nuss. *Opt. Lett.*, 20 (16), 1716 (1995). Since then, THz imaging methods have been rapidly evolving due to advances in THz sources, detectors, and device fabrication methods. The simplest and most prevalent THz imaging method is the use of a single transmitter and detector pair wherein an image is obtained on a point-by-point basis by scanning the object through the THz beam which is focused by a parabolic mirror. Using this method, THz images of macroscopic objects have been obtained (see, Ja-Yu Lu et al., *IEEE Photonics Technol. Lett.*, 17 (11), 2406-2408 (2005); T. Löffler et al., *Appl. Phys. Lett.*, 90, 091111 (2007); I. S. Gregory et al., *Appl. Phys. Lett.* 86, 204104 (2005)) and extended to THz tomography. See, D. M. Mittleman et al., *Opt. Lett.* 22. 904 (1997).

Another approach to imaging known as THz synthetic aperture imaging has been investigated. Such methods require the THz amplitude and phase measured from multiple positions or from multiple beam paths to reconstruct the image. Synthetic phased array THz imaging uses arrayed optical mirrors to reconstruct diffraction-limited THz images. See, J. O'Hara and D. Grischkowsky, *Opt. Lett.* 27, 1070-1072 (2002). Image resolution can be improved when many individual images are superimposed.

Rapid THz spectroscopic data collection and image acquisition requires a faster scanning/modulation method.

SUMMARY OF THE INVENTION

Current technology for continuous wave THz spectrometers requires a method for scanning the THz waveform to determine both the amplitude and phase of the THz wave. Most CW and pulsed THz systems use a scanning delay line (15-300 Hz repetition rate) to modulate the phase of the THz wave. Typically, this is accomplished by mechanically scanning a mirror system (so called mirror shakers) at a rate of ~300 Hz (see for example I. S. Gregory et al., *Appl. Phys. Lett.* 86, 204104 (2005); Yun-Sik Jin et al., Review of Scientific Instruments, 78, 023101 (2007)). The modest scanning rate is due to inertia of the mirrors. U.S. Pat. No. 7,239,775 discloses a system of a pair of rotation mirrors providing nanosecond delay ranges at a repetition rate of hundreds of hertz. Another approach, asynchronous optical sampling (Takeshi Yasui et al., *Appl. Phys. Lett,* 87, 061101 (2005); A. Bartels et al., Review of Scientific Instruments, 78, 035107 (2007)) results in multikilohertz scan rates. However, rapid THz spectroscopic data collection and image acquisition requires a faster scanning/modulation method.

To solve the rapid scanning problem, in at least one embodiment the present invention provides electronic scanning methods and apparatus which generate data more quickly than prior art methods and apparatus.

In at least one embodiment a rapid scanning continuous wave THz imaging system is provided that can acquire the THz waveform at a rate of 500 kHz. This represents a 1000+ times increase in imaging speed compared to time-domain systems with 300 Hz scanning mirrors.

In a further embodiment a system is provided that operates at a single THz frequency within a band of 0.1-3 THz. The system modulates the THz waveform at 500 kHz and averages 100 waveforms (corresponding to 0.2 ms total time integration) to improve the signal-to-noise. Consequently, individual pixels in an image can be acquired at a rate of roughly 5000 pixels per second. In an embodiment wherein for example the THz system in accordance with the present invention uses 10 transmitter and receiver pairs, the total imaging rate is roughly 50,000 pixels per second. Consequently, a 10 square foot area can be imaged in roughly 200 seconds with 1 mm spatial resolution.

In still a further embodiment a homodyne two dimensional terahertz interferometric imaging system is provided. CW terahertz radiation is generated by photomixing the infrared outputs of two semiconductor lasers.

BRIEF DESCRIPTION OF THE DRAWINGS

To assist those of ordinary skill in the relevant art in making and using the subject matter hereof, reference is made to the appended drawings, wherein.

Figure 1:
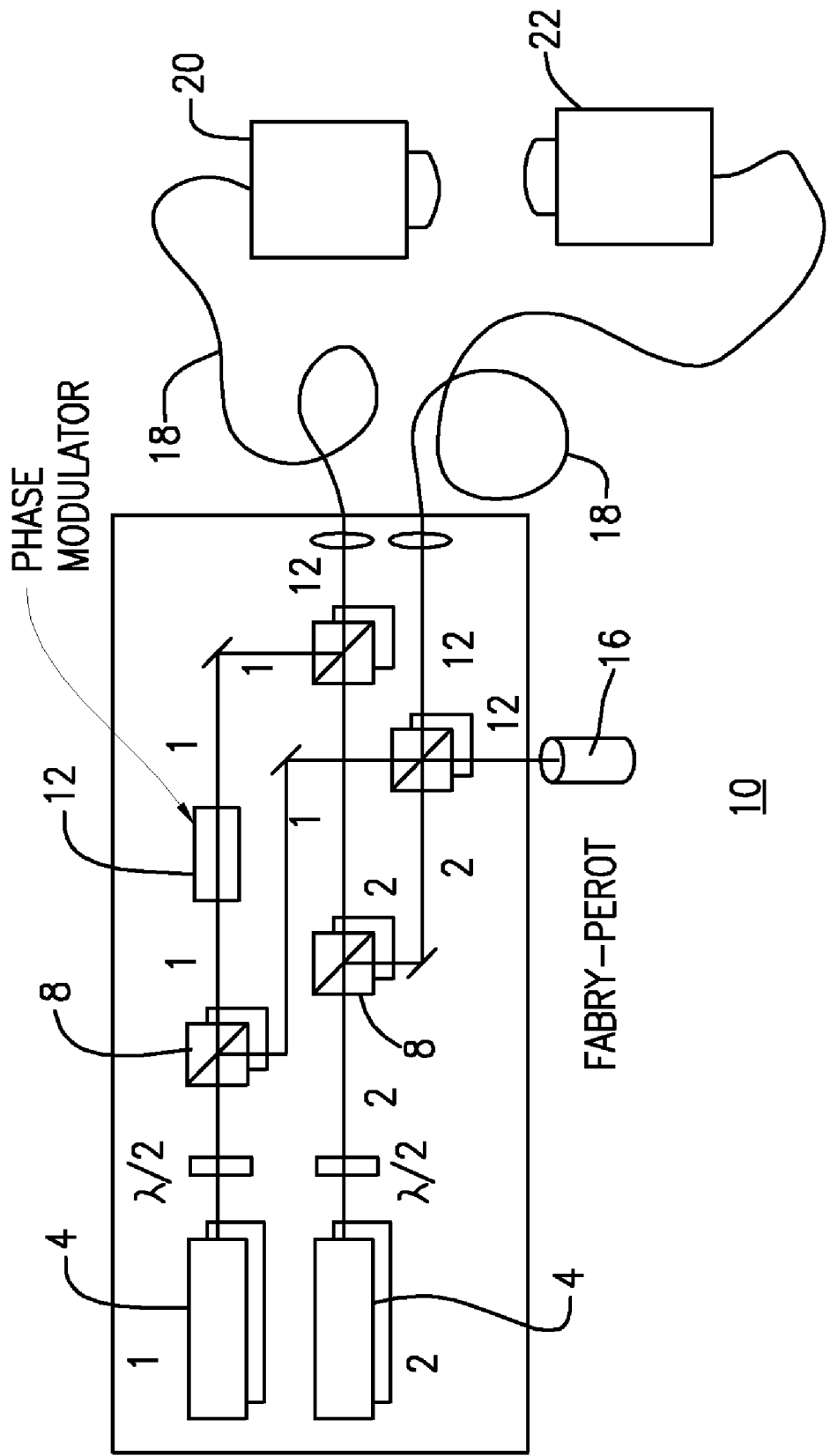
FIG. 1 depicts a schematic of an electronically controlled Lithium Niobate phase modulator system in accordance with at least one embodiment of the present invention.

It should be noted that the appended drawings illustrate only typical embodiments of this invention and are therefore not to be construed as limiting of its scope, for the invention may admit to other equally effective embodiments. Where possible, identical reference numerals have been inserted in the figures to denote identical elements.

DETAILED DESCRIPTION OF THE INVENTION

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

Interferometric imaging can be employed to detect the THz electric field at multiple locations. Interferometric imaging typically employs an aperiodic array of detectors. Being illuminated with THz radiation, the target reflects a part of incident radiation towards the detector array. The intensity and phase of the reflected electric field depends on the shape and the reflectivity of the target. With the amplitude and phase of THz field obtained at the point of each individual detector, detector pairs must be correlated and then the image is reconstructed through Fourier inversion (see, A. R. Thompson, et al., "Interferometry and Synthesis in Radio Astronomy"; J. F. Federici et al., Appl. Phys. Lett. 83, 2477 (2003)), $$\sigma_E(\xi, \eta) = \sum_{l=1}^{N(N-1)/2} [\text{Re}(A_l e^{i\Delta\phi_l})\cos(k(u_l\xi + v_l\eta)) - \text{Im}(A_l e^{i\Delta\phi_l})\sin(k(u_l\xi + v_l\eta))] \quad (1)$$

where $\sigma_E$ is the time-averaged intensity of the source, $u_l=(x_n-x_m)$ and $v_l=(y_n-y_m)$ are the x- and y-separations (baselines) between two detectors m and n located at the points $(x_m,y_m)$ and $(x_n,y_n)$, k is the wave number, and N is the number of detectors in the array. For the detector pair mn, the product of electric field amplitudes is $A_l=E_m E_n$ and the phase difference is $\Delta\phi_l=\phi_m-\phi_n$. Also, new variables $\xi=x'/Z_0$ and $\eta=y'/Z_0$ are introduced for the point (x',y') on the source surface, and $Z_0$ is the distance between the source and the detector array.

Previously, both simulations (see, J. F. Federici et al., Appl. Phys. Lett. 83, 2477 (2003)) and experimental results (see, A. Bandyopadhyay et al., J. Opt. Soc. Am. A, 23, 1168 (2006); A. Sinyukov et al., Proc. SPIE 6373, 63730K-1 (2006); A. Sinyukov et al., Proc. SPIE 6549, 654909-1 (2007)) of one-dimensional and two-dimensional interferometric imaging have been demonstrated.

In interferometric imaging CW radiation concentrated in narrow lines can be employed. Therefore, THz radiation can potentially propagate long distances in the atmosphere and stand-off detection can be realized, which is challenging with pulsed THz systems mostly due to water vapor absorption. In addition, interferometric imaging can be performed with a limited number of detectors, thus reducing the image cost and providing improved imaging rates. With rapid phase modulation, a whole two-dimensional interferometric image can be obtained in as little as 3 min using only one detector. If a larger number of detectors were used, the same image could be acquired in less than 1 second.

Now referring to FIG. 1 a rapid scanning continuous wave terahertz spectroscopy system 10 in accordance with one embodiment of the present invention includes one or more infrared light generators 4, beam splitters 8, a phase modulator 12, an interferometer 16 and a THz emitter 20 and THz receiver 22.

Infrared light generators 4 may be any suitable means of generating a signal or terahertz frequency such as but not limited to a laser. For example, a distributed feedback (DFB) laser may be employed. In accordance with one embodiment THz radiation is generated at the beating frequency of two Littman external cavity diode lasers (Sacher Lion TEC520) operating at 0.78 μm and detuned to 0.6-1 nm (which corresponds to 0.3-0.95 THz). The output of each laser 4 is evenly split using a first pair of beam splitters 8. The laser beams (identified as 1 and 2 in FIG. 1) are mixed together and recombined with another pair of beam splitters 8 and coupled into fibers 18 and delivered to low-Temperature-Grown GaAs bowtie-type photo-conductive dipole antennae (PDA) used as both THz emitter and receiver 20. The total optical power in both channels is ~12 mW. A bias of 20 V DC is applied to power the THz emitter 20.

The splitting of the laser beams 1 and 2 is necessary to insert the electronic phase modulator 12 into one of the beams 1 and/or 2. The phase modulator 12 is an important feature of the system 10 of the present embodiment. The present inventors have discovered that mechanical scanning of the THz transmitter-receiver separation used to detect the THz field and to obtain its amplitude and phase at every point of the detector array which is necessary to reconstruct the image with Eq. 1 was slow, and due to the slowness of mechanical scanning, the time to acquire a THz waveform was about two hours. Likewise, most CW and pulsed THz systems use a scanning delay line (15-300 Hz repetition rate) to modulate the phase of the THz wave. The present inventors have found that applying an AC voltage to the electronic phase modulator 12 permits direct modulation of the phase ($\Delta\phi$) and obtains the THz amplitude and phase with a digital lock-in amplifier (not shown) at high rates. A 100 kHz AC voltage of 4 V may be amplified by a factor of 20 with an amplifier (for example, FLC Electronics, Model F20AD), and is applied to the phase modulator 12 (for example, New Focus 4002). The THz amplitude and phase are then obtained with the digital lock-in amplifier (not shown) (for example, EG&G instruments, Model 7260) in a few seconds.

The electronically controlled phase shifter replaces a mechanically scanning mirror and delay line or the mechanical scanning of the transmitter/receiver distance. Its operation can be understood by recognizing that the phase and amplitude of the generated THz wave is a result of the multiplication or mixing of the two infrared laser beams in the THz source. The THz wave is proportional to the frequency and phase difference of the two infrared waves:

$$E_{THz} \sim E_1 \square E_2 \sim E_{1o} \sin(\omega_1 t + \phi_1) \square E_{2o} \sin(\omega_2 t + \phi_2) \quad (1)$$

Multiplying out the right-hand side of Eq. (1) gives $$E_{THz} \sim E_{1o} \square E_{2o} \cos((\omega_1 - \omega_2)t + (\phi_1 - \phi_2)) \quad (2)$$

Breaking the above equation into frequency and phase portions gives $$E_{THz} \sim E_{1o} \square E_{2o} [\cos((\omega_1 - \omega_2)t)\cos(\phi_1 - \phi_2) - \sin((\omega_1 - \omega_2)t)\sin(\phi_1 - \phi_2)] \quad (3)$$

The frequency of the THz wave is given by the frequency difference of the two infrared lasers and the phase of the THz wave is given by the relative phase difference of the two infrared lasers. By applying a time-varying voltage to the phase shifter, the phase of one infrared laser beam $\phi_1(t)$ can be modulated and therefore directly modulate the phase of the radiated THz wave. By applying a sufficient voltage such that the phase of the THz radiation varies by $2\pi$, one can use a lock-in amplifier (or digitizer) to digitize the measured THz waveform and directly measure the phase and amplitude of the THz wave.

The generated THz wave can be presented as a product of electric fields, $$E_{THz} \sim E_1 \square E_2 \sim E_1 \sin(\omega_1 t + \phi_1) E_2 \sin(\omega_2 t + \phi_2) \sim E_1 E_2 [\cos(\Delta\phi t)\cos(\Delta\phi t) - \sin(\Delta\omega t)\sin(\Delta\phi)], \quad (2)$$

where $\Delta\omega = \omega_1 - \omega_2$, $\Delta\phi = \phi_1 - \phi_2$, $E_1$ and $E_2$ are the amplitudes of electric fields at the frequencies $\omega_1$ and $\omega_2$ respectively.

Without being restricted to a single theory, it is believed that this rapid scanning enables the THz waveform (and hence the phase and amplitude) at each detector position to be measured in <30 ms (i.e. compatible with an eventual video rate system).

Figure 2:
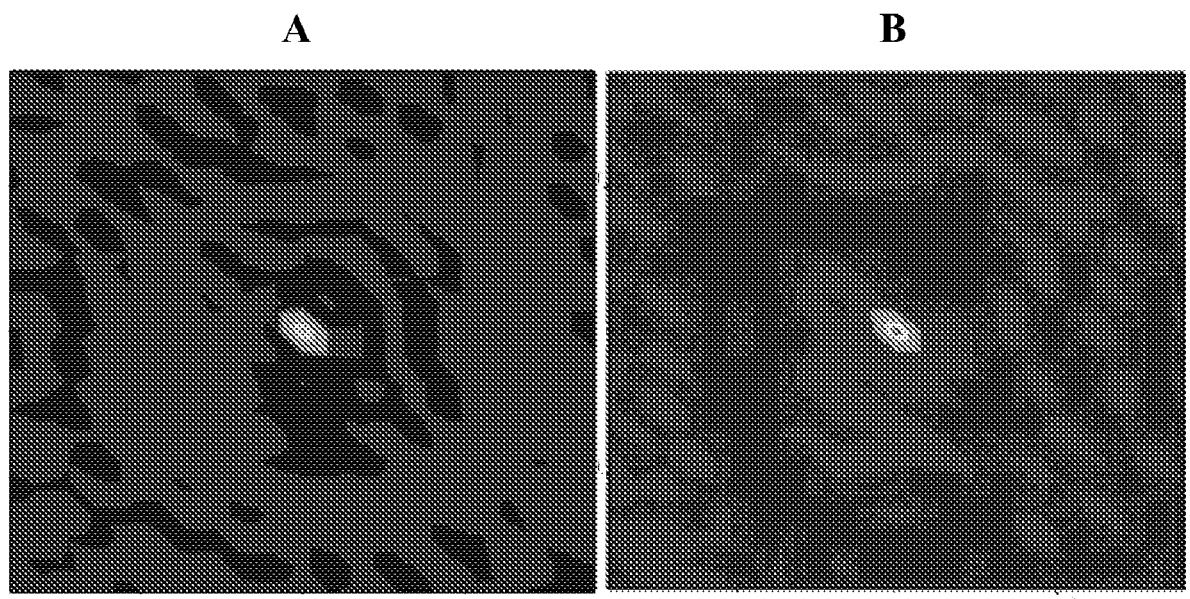
FIG. 2A depicts a 2-D THz interferometric image of a THz source in accordance with at least one embodiment of the present invention.
FIG. 2B depicts a 2-D THz interferometric image of the THz source of FIG. 2A hidden behind a thick bookbag in accordance with at least one embodiment of the present invention.

Now referring to FIGS. 2A and 2B, employing the presently disclosed methods interferometric images of a point THz source were obtained. Using computer controlled translation stages, a single THz receiver is moved to different locations to mimic the performance of a 2-D imaging array. Ordinarily, the 2-D imaging array would be comprised of N individual receivers. However, in demonstrating the presently disclosed methods, only one receiver was available. Consequently, acquiring an image is a result of physically moving an individual detector to N different positions (~1-2 seconds per position). In this configuration, an image typically required at least several minutes to acquire. Using the apparatus of FIG. 1, the 2-D THz images of FIGS. 2A and 2B were acquired in 2 minutes. Using a mechanical scanning method, a comparable image would require 2 hours. If N detectors were used rather than a single detector, the THz image could be acquired in less than 1 second with the present electronic phase modulation method.

FIG. 2A depicts a THz point source. FIG. 2B is the same point source hidden behind a thick nylon bookbag. The array is equivalent to 64 detector positions. The applied voltage to the phase modulator was 120V at a frequency of 100 kHz. The time-constant (averaging) of the lock-in amplifier was set to 1 second. The distance between the THz emitter and the detector array was 80 cm. The ECDL power from both lasers on the THz transmitter was ~7 mW while the power on the receiver was roughly ~5.5 mW. The distance between the THz emitter and detector was ~80 cm. If 64 detectors were used rather than a single detector, the THz image could be acquired in less than 1 second with the present electronic phase modulation method.

Figure 3:
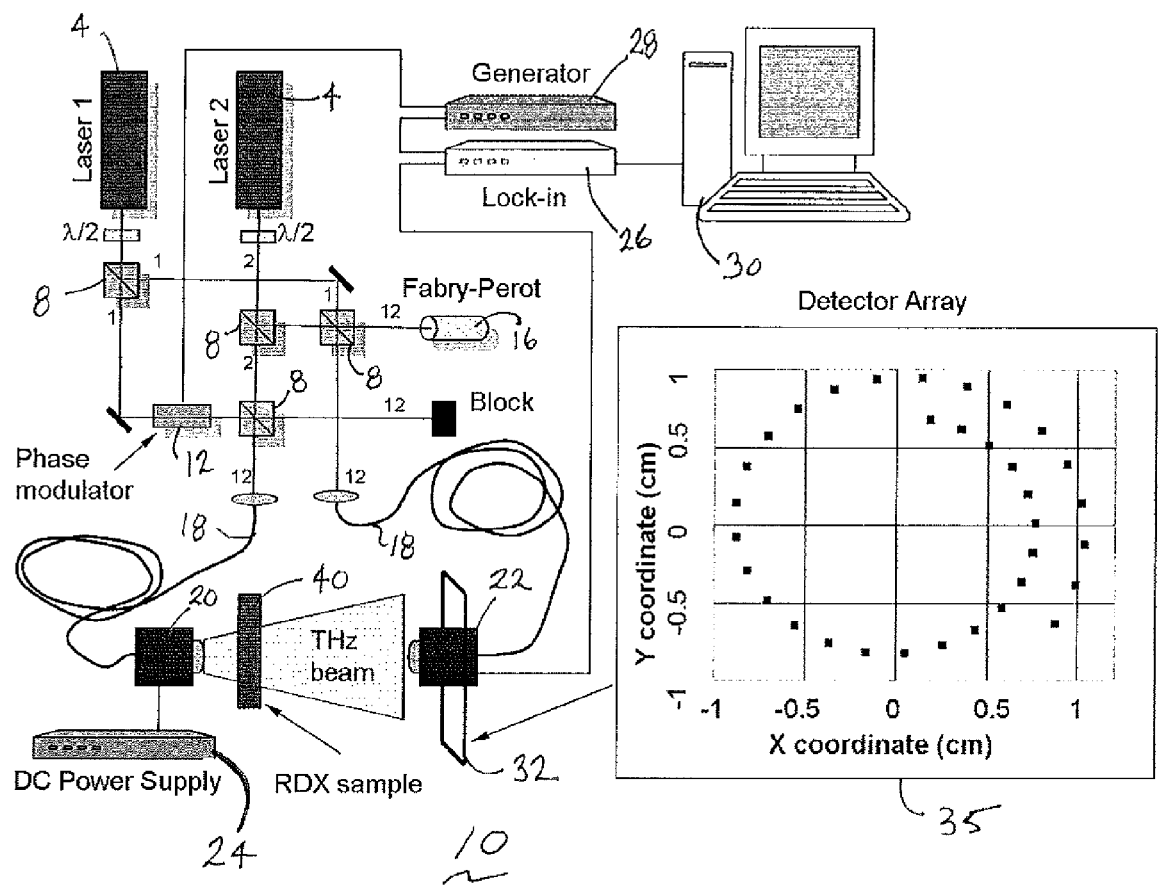
FIG. 3 depicts a schematic of a homodyne interferometric imaging system in accordance with at least one embodiment of the present invention.

Now referring to FIG. 3 a rapid scanning continuous wave homodyne terahertz interferometric imaging system 10 in accordance with another embodiment includes one or more THz generators 4, beam splitters 8, a phase modulator 12, an interferometer 16, a THz emitter 20 and receiver 22, DC power supply 24, lock-in amplifier 26, generator 28 and computer 30.

The system according to FIG. 3 was employed to conduct an experiment wherein THz radiation was generated at the beating frequency of two Littman external cavity diode lasers (Sacher Lion TEC520) operating at 0.78 µm and detuned to 0.6-1 nm (which corresponds to 0.3-0.95 THz). The output of each laser was evenly split using the first pair of beam splitters 8. The laser beams (identified as 1 and 2 in FIG. 3) were mixed together and recombined with another pair of beam splitters 8 and coupled into fibers 18 and delivered to low-Temperature-Grown GaAs bowtie-type photo-conductive dipole antennae (PDA) used as both THz emitter 20 and receiver 22. The total optical power in both channels was ~12 mW. A bias of 20 V DC was applied by DC power supply 24 to power the THz emitter 20. A single THz detector 22 was used. The detector 22 was mounted on an X-Y computer controlled stage 32 (Newport ESP 300) and scanning of stage 32 allowed the placement of the THz detector 22 at each point along a spiral path to simulate the performance of a detector array by movement of a single THz detector 22. The spiral geometry 35 of the detector array is also presented in FIG. 3. The amplitude of the AC voltage applied to the phase modulator 12 corresponds to $V_\pi$ for this model at 780 nm. Applying an AC voltage to the electronic phase modulator 12 permitted direct modulation of the phase ($\Delta\phi$) and obtained the THz amplitude and phase with a digital lock-in amplifier 26 at high rates. A 100 kHz AC voltage of 4 V was amplified by a factor of 20 with an amplifier 26 (FLC Electronics, Model F20AD), and was applied to the phase modulator 12 (New Focus 4002). The THz amplitude and phase were then obtained with the digital lock-in amplifier 26 (EG&G instruments, Model 7260) in a few seconds.

With the detector array of 32 positions and a time constant of 5 s, it took about 3 min. to acquire an image.

Figure 4:
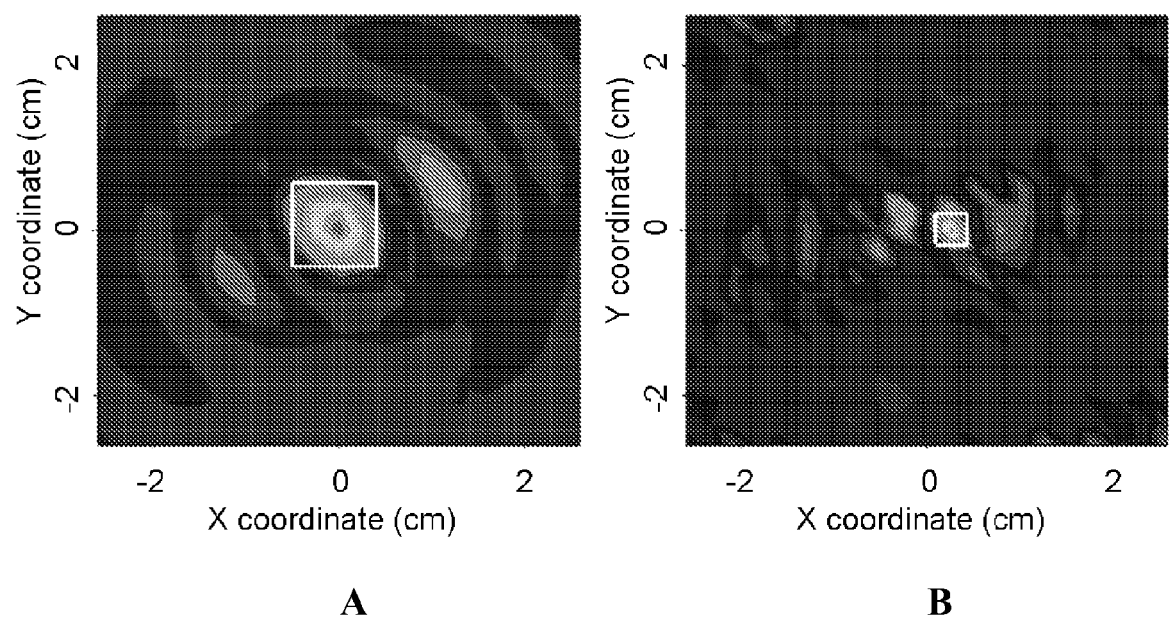
FIG. 4A depicts terahertz interferometric images of a point source at 0.34 THz in accordance with at least one embodiment of the present invention, wherein white squares indicate the integration area.
FIG. 4B depicts terahertz interferometric images of a point source at 0.8 THz in accordance with at least one embodiment of the present invention, wherein white squares indicate the integration area.

Now referring to FIGS. 4A and 4B, interferometric images of a point source at 0.34 THz and 0.8 THz are shown, respectively. No image correction algorithms were applied. Therefore, some artifacts of Fourier inversion (sidelobs) can be observed in these images. The resolution of interferometric imaging depends on the wavelength and the maximum separation between detectors $b_{max}$: $\theta_{min} = \lambda/b_{max}$. Therefore, the higher the THz frequency, the better the image resolution. This dependence can be seen in FIGS. 4A and 4B.

As a practical example of this method, spectral interferometric images of a point THz source transmitting through a C-4 sample 40 were obtained using the system of FIG. 3. The distance between the THz emitter 20 and detector 22 was ~25 cm. The C-4 sample 40 was 1 mm thick and ~4 cm in diameter. The sample 40 was inserted between the THz emitter 20 and detector 22, and images at several frequencies were obtained. The experiment was performed in open air. The THz frequencies for imaging were selected to be away from water absorption lines. See, Martin van Exter et al., *Opt. Lett.*, 14(20), 1128 (1989). In order to take into account the strong frequency dependent response of the CW THz system, the image without the sample (reference image) together with the image when the sample was inserted (signal image) were acquired at every frequency. Then, the area scaled according to the THz frequency (indicated by the white squares in FIGS. 4A and 4B) under the main peak was calculated for both images and the ratio (Signal image)/(Reference image) provided the relative transmission T of the C-4 sample 40 at each frequency. Absorbance A can be calculated as $A=\log(1/T)$.

Figure 5:
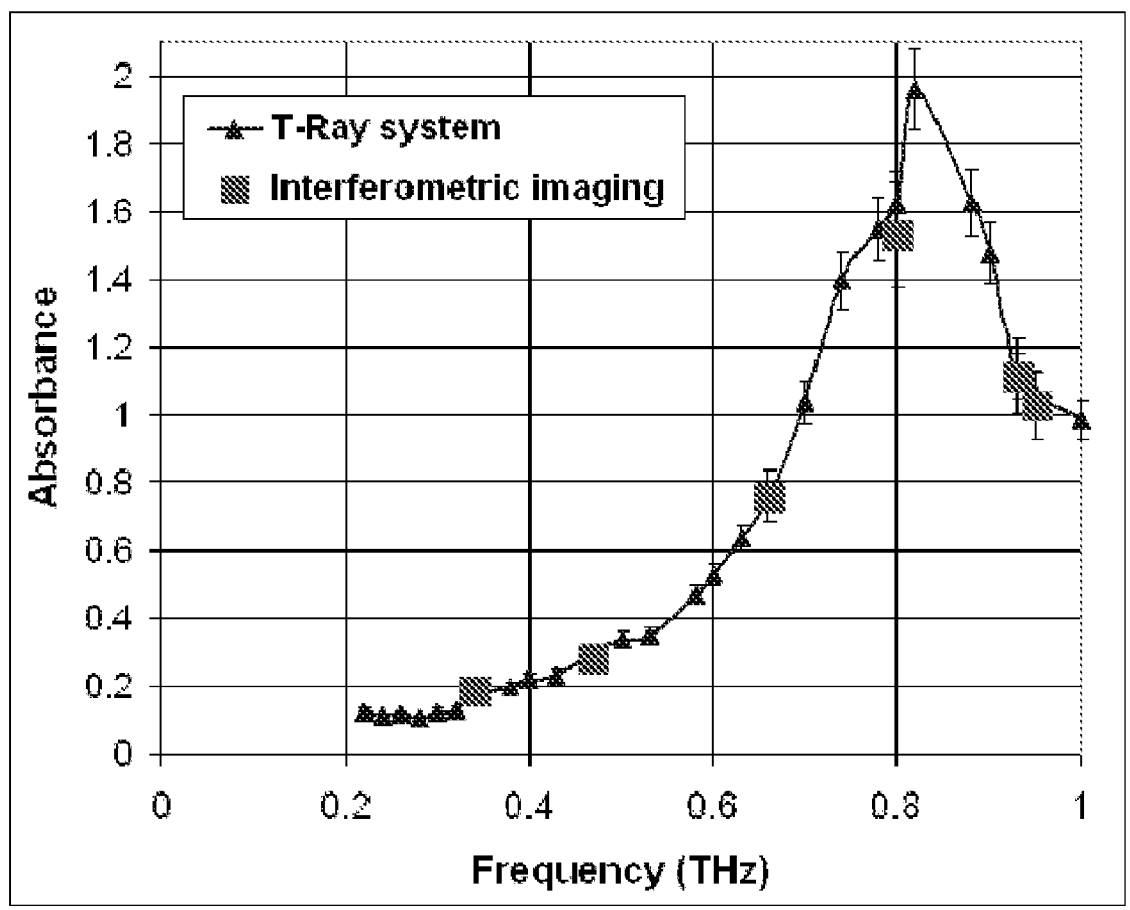
FIG. 5 is a graphical representation of absorbance of a C-4 sample obtained with interferometric imaging (squares) and with a pulsed T-ray system (solid line and triangles) in accordance with at least one embodiment of the present invention.

Now referring to FIG. 5, absorbance of the C-4 sample 40 as a function of THz frequency, based on the integrated central areas of the images is presented. The absorption peak of RDX at 0.82 THz can be recognized (see, W. R. Tribe et al., *Proc. SPIE* 5354 168 (2004); F. Huang et al., *Appl. Phys. Lett.*, 85, 5535 (2004); H. Liu et al., *Opt. Express* 14, 415 (2006)). This result is in a good agreement with spectral data obtained with a pulsed T-ray system for the same sample 40. The maximum possible phase modulation frequency is limited mostly by the response of the photoconductive antenna THz modules. Also, performance of interferometric imaging system 10 can be improved significantly with a higher optical power: the time constant can be reduced and the image can be produced in less than 1 second. It will be understood that in a full interferometer system, multiple detectors will be used simultaneously; therefore, the imaging time can be reduced further compared to a single detector that is translated to multiple positions.

Figure 6:
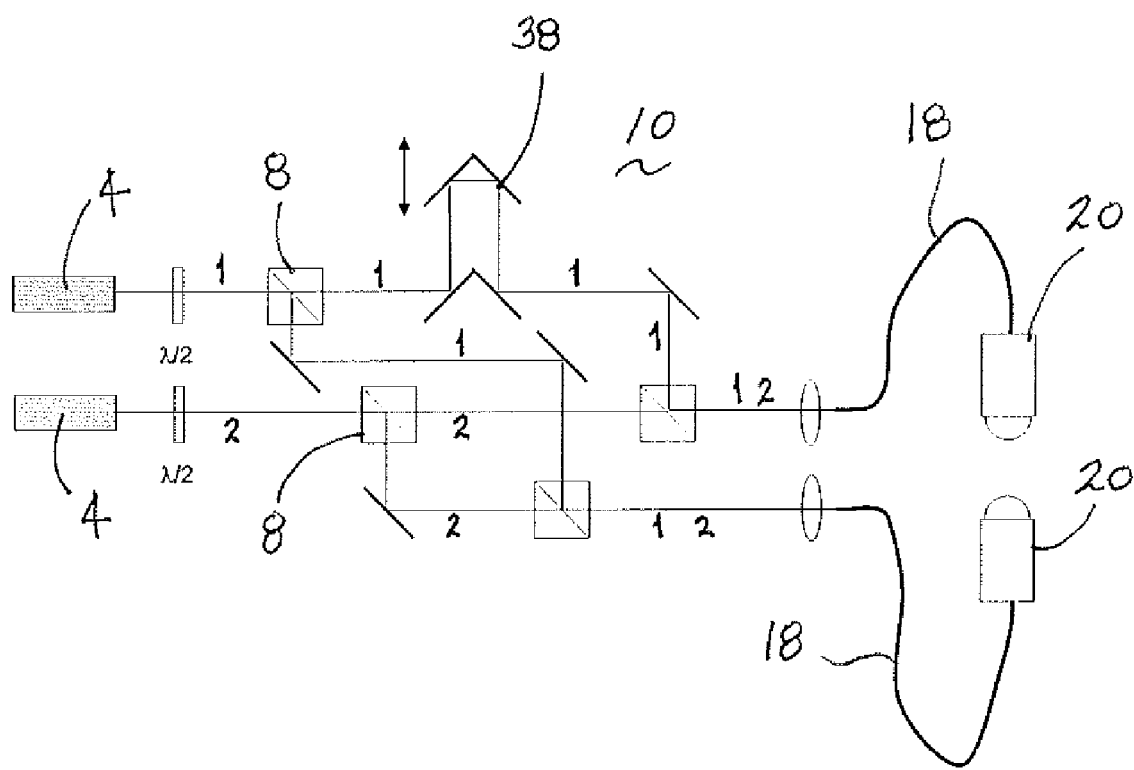
FIG. 6 depicts an interferometric imaging system in accordance with at least one embodiment of the present invention.

Now referring to FIG. 6, in another embodiment a system 10 adapted to achieve a rapid phase modulation comprises a scanning mirror delay to delay only one of the laser beams 1 or 2. In accordance with this embodiment a scanning mirror 38 is employed in place of a phase modulator. In current state of the art apparatus that employ a scanning mirror, the mirror needs to move distances of about 1 cm. This large distance and inertia mass of the mirror restricts the rate at which the mirror can be scanned to ~300 Hz. However, in the present embodiment, the distances required to move are only about 10 μm. Since this distance is much smaller than the 1 cm required for in the current state of the art practice, a much faster scanning mirror can be employed. In accordance with one embodiment a PZT stack is used to oscillate the mirror at tens of kilohertz frequencies.

The present inventions can be applied in any environment where rapid scanning of samples is necessary or desirable, including but not limited to airports, arenas, schools, office buildings, government buildings, military installations, mobile military units, vehicles and the like.

Applicants have attempted to disclose all embodiments and applications of the described subject matter that could be reasonably foreseen. However, there may be unforeseeable, insubstantial modifications that remain as equivalents. While the present invention has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

All references cited herein are incorporated fully by reference.

What is claimed is:

1. A method of analyzing a sample employing rapid scanning continuous wave terahertz spectroscopy comprising:
   providing at least two individual laser beams containing THz radiation, splitting each of the individual laser beams, mixing the split laser beams, recombining the laser beams and coupling the laser beams into fibers,
   delivering a laser beam to each of a THz receiver and a THz transmitter wherein at least one of the THz receiver and THz transmitter comprise a photo-conductive dipole antennae (PDA);
   modulating the phase of THz radiation to be introduced to a sample using an electronic phase modulator;
   introducing phase-modulated THz radiation to the sample, receiving the THz radiation transmitted through the sample; and
   collecting spectral data of the received THz radiation.

2. The method of claim 1 wherein the PDA is a low-temperature-grown GaAs bowtie-type photo-conductive dipole antennae.

3. The method of claim 1 further comprising applying a bias of between 0.1-100V DC to modulate a phase modulator.

4. The method of claim 1 wherein the THz radiation in the at least two individual laser beams is in the range of 0.1-10 THz.

5. The method of claim 1 comprising applying an AC voltage to the phase modulator.

6. The method of claim 1 further comprising obtaining images at more than one THz frequency.

7. The method of claim 1 further comprising the step of comparing spectral information obtained to known data.

8. The method of claim 1 wherein the sample optionally includes an explosive material.

9. The method of claim 1 wherein the sample is a container.

10. The method of claim 1 wherein the sample is luggage.

11. A rapid scanning continuous wave terahertz spectroscopy apparatus comprising at least one THz generator, at least one THz transmitter configured to introduce a THz signal to a sample, a receiver configured to receive THz radiation transmitted through the sample; at least one beam splitter, and at least one electronic phase modulator operable to modulate the phase of THz radiation to be introduced to a sample.

12. The apparatus of claim 11 further comprising a device adapted to collect spectral data from the received THz radiation.

13. The apparatus of claim 11 comprising a device adapted to compare an absorption value of the received THz radiation to a known absorption value.

14. The apparatus of claim 11 further comprising a lock-in amplifier operable to obtain at least one of THz amplitude and phase.

15. The apparatus of claim 11 further comprising a movable stage to which the THz receiver is operably connected.

16. The apparatus of claim 11 comprising a plurality of THz transmitter and receiver pairs.

17. A system employing the apparatus of claim 11 adapted to operate at a single THz frequency within a band of 0.1-10 THz and further adapted to modulate a THz waveform at 500 kHz.

* * * * *